US007715608B2

(12) United States Patent
Vaz et al.

(10) Patent No.: US 7,715,608 B2
(45) Date of Patent: May 11, 2010

(54) SYSTEM AND METHOD FOR 3D VISUALIZATION OF LUNG PERFUSION OR DENSITY AND STATISTICAL ANALYSIS THEREOF

(75) Inventors: Michael Vaz, Hillsboro, OR (US); Atilla Peter Kiraly, Plainsboro, NJ (US); Carol L. Novak, Newtown, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 954 days.

(21) Appl. No.: 11/182,913

(22) Filed: Jul. 15, 2005

(65) Prior Publication Data
US 2006/0056691 A1    Mar. 16, 2006

Related U.S. Application Data

(60) Provisional application No. 60/600,257, filed on Aug. 10, 2004.

(51) Int. Cl.
*G06K 9/00* (2006.01)
(52) U.S. Cl. .................................. 382/131; 382/130
(58) Field of Classification Search ................. 382/130, 382/131
See application file for complete search history.

(56) References Cited

U.S. PATENT DOCUMENTS

| 5,687,208 | A | 11/1997 | Bae et al. | |
|---|---|---|---|---|
| 6,083,162 | A | 7/2000 | Vining | |
| 6,650,928 | B1 * | 11/2003 | Gailly et al. | 600/425 |
| 2002/0131625 | A1 * | 9/2002 | Vining et al. | 382/128 |
| 2003/0234781 | A1 * | 12/2003 | Laidlaw et al. | 345/419 |
| 2005/0283070 | A1 * | 12/2005 | Imielinska et al. | 600/425 |

OTHER PUBLICATIONS

Niethammer et al., "A New Approach to Diagnosis of Pulmonary Embolism using Multi-Slice CT", 2001, SPIE, Proceedings of SPIE vol. 4321, 244-252.*
Arakawa et al., "Air Trapping on CT of Patients with Pulmonary Embolism", May 2002, American Journal of Roentgenology, AJR:178, 1201-1207.*
Flohr et al., "Fast image filters as an alternative to reconstruction kernels in Computed Tomography", 2001, SPIE, Proceedings of SPIE vol. 4322, 924-933.*

* cited by examiner

*Primary Examiner*—Vikkram Bali
*Assistant Examiner*—Katrina Fujita

(57) ABSTRACT

A system and method for 3D visualization of a pair of lungs are provided. The method comprises: segmenting image data of the pair of lungs and lung parenchyma; generating a 3D map as a function of the segmented image data; and rendering the 3D map as a color-coded semi-transparent 3D volume, wherein an opaque region highlights an area of interest.

29 Claims, 12 Drawing Sheets

SYSTEM AND METHOD FOR 3D VISUALIZATION OF LUNG PERFUSION OR DENSITY AND STATISTICAL ANALYSIS THEREOF

CROSS-REFERENCE TO RELATED APPLICATION

This application claims the benefit of U.S. Provisional Application No. 60/600,257, filed Aug. 10, 2004, a copy of which is herein incorporated by reference.

BACKGROUND OF THE INVENTION

1. Technical Field

The present invention relates to medical image analysis, and more particularly, to a system and method for three-dimensional (3D) visualization of lung perfusion or density and a method for analyzing lung perfusion or density distribution in patients for diagnosis.

2. Discussion of the Related Art

A pulmonary embolism occurs when a piece of a blood clot from a deep vein thrombosis (DVT) breaks off and travels to an artery in a lung where it blocks the artery, damages the lung and puts a strain on the heart. This short-term complication is potentially life threatening and occurs in about ten percent of patients with acute DVT events. It may be even more common than generally realized because a majority of embolisms occur without symptoms.

The majority of people recover fully from a DVT and pulmonary embolism. However, a large pulmonary embolism can block almost all of the blood flow to a portion of the lungs and cause sudden death. In addition, a pulmonary embolism can put a severe strain on the heart. After ischemic heart disease and stroke, a pulmonary embolism is the third leading cause of death from heart disease. Yet it may be the most common preventable cause of death in hospitals.

Given the nature of pulmonary embolism, timely diagnosis is critical. However, it is also important to assess how emboli affect blood flow in the lungs. Recently, there has been a growing research interest in automatic methods for detection of pulmonary emboli from high-resolution computed tomography angiography (CTA). In addition, there has been an interest in methods for visualizing and assessing the extent and location of perfusion deficits caused by a pulmonary embolism. Such techniques utilize multi-slice computed tomography (CT) machines that routinely generate 600 or more two-dimensional (2D) slices per patient to identify segmental and sub-segmental emboli. However, this can be time-consuming and does not lend itself to immediate visualization of lung perfusion.

Recently, however, researchers have presented an experimental method for 2D visualization of lung perfusion within the parenchyma following administration of intravenous contrast. This method produces a 2D visualization of color-coded parenchymal perfusion overlaid on an original CT image. While this information does convey some useful information, it is difficult to keep track of regions of abnormal perfusion. Further, if there is a pulmonary embolus proximal to such a region, keeping track of where it is located with respect to the region is arduous.

Accordingly, there is a need for a technique of viewing a 3D map for highlighting areas of diminished or abnormal perfusion or abnormal regions within the parenchyma thereby enabling the identification of pulmonary emboli or other abnormalities and a technique for analyzing such data for diagnosis.

SUMMARY OF THE INVENTION

The present invention overcomes the foregoing and other problems encountered in the known teachings by providing a system and method for 3D visualization of lung perfusion or density that allows a medical practitioner to examine the entire lung volume in a single view and a method for analyzing lung perfusion or density distribution in patients for diagnosis.

In one embodiment of the present invention, a method for 3D visualization of a pair of lungs, comprises: segmenting image data of the pair of lungs and lung parenchyma; generating a 3D map as a function of the segmented image data; and rendering the 3D map as a color-coded semi-transparent 3D volume, wherein an opaque region highlights an area of interest.

The 3D map is one of a perfusion map or a density map and may be computed by one of adaptive smoothing or texture filtering. The area of interest indicates a region of abnormal perfusion or density. The region of abnormal perfusion is due to an embolus.

The method further comprises: generating a histogram of the rendered 3D map; determining whether the histogram indicates a positive or negative presence of embolus; and classifying embolus as one of acute or chronic.

In another embodiment of the present invention, a method for 3D visualization of lung perfusion, comprises: segmenting image data of lung parenchyma; generating a perfusion map of the segmented image data; and rendering the perfusion map as a color-coded semi-transparent 3D volume, wherein an opaque region of perfusion is visible.

The step of generating a perfusion map of the segmented image data comprises: segmenting the lung parenchyma; performing a local smoothing; and determining local-neighborhood mean densities of the lung parenchyma. The step of segmenting the lung parenchyma comprises: segmenting a volume of the pair of lungs from a thoracic volume; identifying airways and blood vessels in the segmented lung volume; and generating a mask of the lung parenchyma by removing the airways and vascular structures from the segmented lung volume.

The step of performing a local smoothing comprises: shifting the image data; masking the shifted image data with the parenchyma mask to obtain a parenchyma image; performing a Gaussian smoothing on the parenchyma mask and image to obtain a smoothed parenchyma a mask and image; masking the smoothed parenchyma image with the parenchyma mask; equalizing the masked smoothed parenchyma image; and shifting the equalized image to generate the perfusion map.

The visible region of perfusion is an indication of one of pulmonary embolus or diffuse lung disease. The image data is acquired using one of a CT, helical CT or MR imaging technique. The method further comprises adjusting a color map to observe high density regions of interest. The visible region of perfusion is one of low perfusion, high perfusion or abnormal perfusion.

In yet another embodiment of the present invention, a system for 3D visualization of a pair of lungs, comprises: a memory device for storing a program; a processor in communication with the memory device, the processor operative with the program to: segment image data of the pair of lungs and lung parenchyma; generate a 3D map as a function of the segmented image data; and render the 3D map as a color-coded semi-transparent 3D volume, wherein an opaque region highlights an area of interest.

The 3D map is one of a perfusion map or a density map and may be computed by one of adaptive smoothing or texture filtering. The area of interest indicates a region of abnormal perfusion or density. The region of abnormal perfusion is due to an embolus.

The processor is further operative with the program code to: generate a histogram of the rendered 3D map; determine whether the histogram indicates a positive or negative presence of embolus; and classify embolus as one of acute or chronic.

In another embodiment of the present invention, a system for 3D visualization of lung perfusion, comprises: a memory device for storing a program; a processor in communication with the memory device, the processor operative with the program to: segment image data of lung parenchyma; generate a perfusion map of the segmented image data; and render the perfusion map as a color-coded semi-transparent 3D volume, wherein an opaque region of perfusion is visible.

When generating a perfusion map of the segmented image data the processor is further operative with the program code to: segment the lung parenchyma; perform a local smoothing; and determine local-neighborhood mean densities of the lung parenchyma. When segmenting the lung parenchyma the processor is further operative with the program code to: segment a volume of the pair of lungs from a thoracic volume; identify airways and blood vessels in the segmented lung volume; and generate a mask of the lung parenchyma by removing the airways and vascular structures from the segmented lung volume.

When performing a local smoothing the processor is further operative with the program code to: shift the image data; mask the shifted image data with the parenchyma mask to obtain a parenchyma image; perform a Gaussian smoothing on the parenchyma mask and image to obtain a smoothed parenchyma mask and image; mask the smoothed parenchyma image with the parenchyma mask; equalize the masked smoothed parenchyma image; and shift the equalized image to generate the perfusion map.

The visible region of perfusion is an indication of one of pulmonary embolus or diffuse lung disease. The image data is acquired using one of a CT, helical CT or MR imaging device. The processor is further operative with the program code to adjust a color map to observe high density regions of interest. The visible region of perfusion is one of low perfusion, high perfusion or abnormal perfusion.

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention will become apparent in the following description, from the drawings and from the claims.

DETAILED DESCRIPTION OF EXEMPLARY EMBODIMENTS

Figure 1:
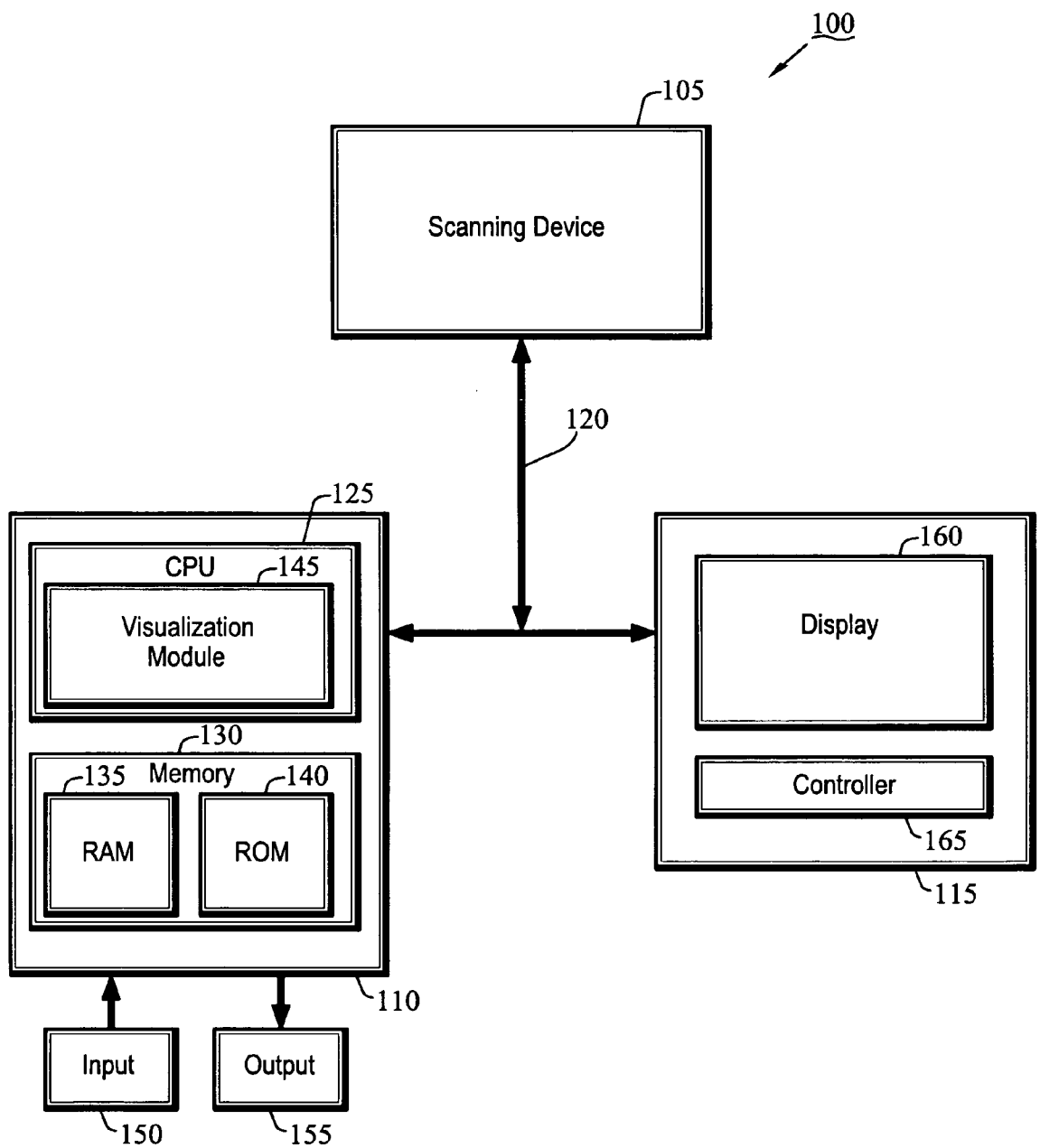
FIG. 1 is a block diagram of a system for 3D visualization of lung perfusion or density according to an exemplary embodiment of the present invention.

FIG. 1 is a block diagram of a system 100 for 3D visualization of lung perfusion or density according to an exemplary embodiment of the present invention. As shown in FIG. 1, the system 100 includes, inter alia, a scanning device 105, a personal computer (PC) 110 and an operator's console 115 connected over, for example, an Ethernet network 120. The scanning device 105 may be a magnetic resonance (MR) imaging device, a CT imaging device, a helical CT device, a positron emission tomography (PET) device, a 2D or 3D fluoroscopic imaging device, a 2D, 3D, or four-dimensional (4D) ultrasound imaging device, or an x-ray device. The scanning device 105 may also be a hybrid imaging device capable of CT, MR, PET or other imaging techniques.

The PC 110, which may be a workstation, portable or laptop computer, a personal digital assistant (PDA), etc., includes a central processing unit (CPU) 125 and a memory 130, which are connected to an input 150 and an output 155. The CPU 125 includes a visualization module 145 that includes one or more methods for 3D visualization of lung perfusion or density.

The memory 130 includes a random access memory (RAM) 135 and a read only memory (ROM) 140. The memory 130 can also include a database, disk drive, tape drive, etc., or a combination thereof. The RAM 135 functions as a data memory that stores data used during execution of a program in the CPU 125 and is used as a work area. The ROM 140 functions as a program memory for storing a program executed in the CPU 125. The input 150 is constituted by a keyboard, mouse, etc., and the output 155 is constituted by a liquid crystal display (LCD), cathode ray tube (CRT) display, or printer.

The operation of the system 100 is controlled from the operator's console 115, which includes a controller 165, for example, a keyboard, and a display 160, for example, a CRT display. The operator's console 115 communicates with the PC 110 and the scanning device 105 so that 2D image data collected by the scanning device 105 can be rendered into 3D data by the PC 110 and viewed on the display 160. It is to be understood that the PC 110 can be configured to operate and display information provided by the scanning device 105 absent the operator's console 115, using, for example, the input 150 and output 155 devices to execute certain tasks performed by the controller 165 and display 160.

The operator's console 115 further includes any suitable image rendering system/tool/application that can process digital image data of an acquired image dataset (or portion thereof) to generate and display 2D and/or 3D images on the display 160. More specifically, the image rendering system may be an application that provides 2D/3D rendering and visualization of medical image data, and which executes on a general purpose or specific computer workstation. Moreover, the image rendering system enables a user to navigate through a 3D image or a plurality of 2D image slices. The PC 110 may also include an image rendering system/tool/application for processing digital image data of an acquired image dataset to generate and display 2D and/or 3D images.

As shown in FIG. 1, the visualization module 145 may also be used by the PC 110 to receive and process digital medical image data, which as noted above, may be in the form of raw image data, 2D reconstructed data (e.g., axial slices), or 3D reconstructed data such as volumetric image data or multi-planar reformats, or any combination of such formats. The data processing results can be output from the PC 110 via the network 120 to an image rendering system in the operator's console 115 for generating 2D and/or 3D renderings of image data in accordance with the data processing results, such as segmentation of organs or anatomical structures, color or intensity variations, and so forth.

Figure 2:
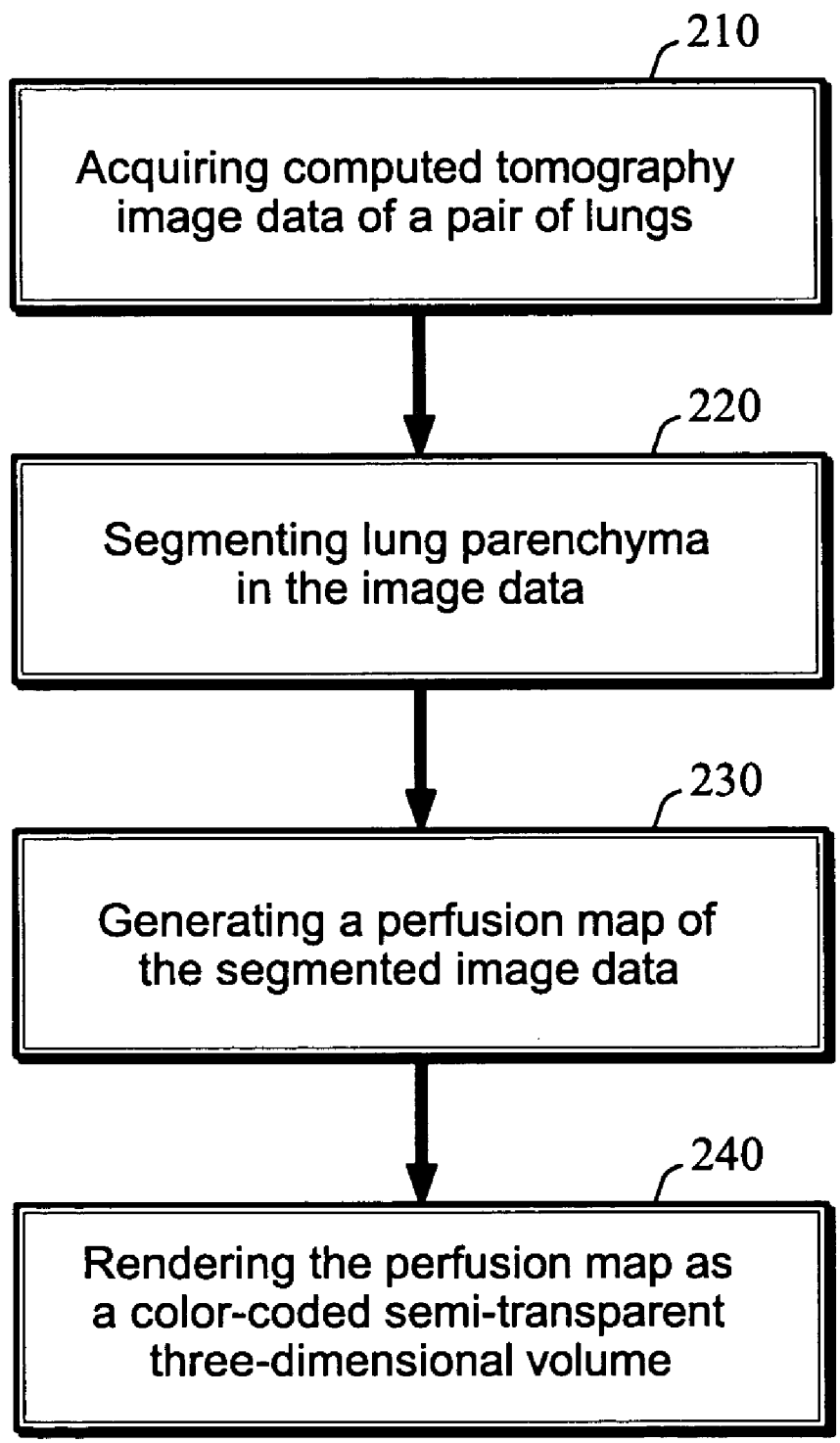
FIG. 2 is a flowchart illustrating a method for 3D visualization of lung perfusion or density according to an exemplary embodiment of the present invention.

FIG. 2 is a flowchart showing an operation of a method for 3D visualization of lung perfusion or density according to an exemplary embodiment of the present invention. As shown in FIG. 2, CT image data is acquired from a pair of lungs inside a patient (210). This is accomplished by using the scanning device 105, in this example a CT scanner, which is operated at the operator's console 115, to scan the patient's lungs thereby generating a series of 2D image slices associated with the lungs. The 2D image slices of the lungs are then combined to form a 3D image. In addition to the lungs, it is to be understood that the CT image data can be acquired from any one of a leg, arm, brain or other body part containing blood vessels. Further, other types of data such as MR image data may be used in accordance with the present invention.

After the CT image data is acquired, the image data of a parenchyma in the pair of lungs is segmented (220). The image data of the parenchyma may be segmented using a conventional segmentation technique such as one that detects the edge or contour of the object to be segmented or one that distinguishes various regions of an ambient image to identify the segmented image. Once the image data has been segmented, a perfusion map of the segmented image data is generated (230).

It is to be understood, however, that in addition to generating a perfusion map in this step, a function of the image data within the segmented image data can be obtained. This function can be any function that is used to output a numerical value based upon local information of the segmented region. For example, a filter that provides high response values to particular textures such as a Gabor filter can be used to generate a map for highlighting particular textures. In addition, the map may be generated by the union of such functions by, for example, combining the perfusion map along with the output of the texture filter to produce a new mapping.

Figure 3A:
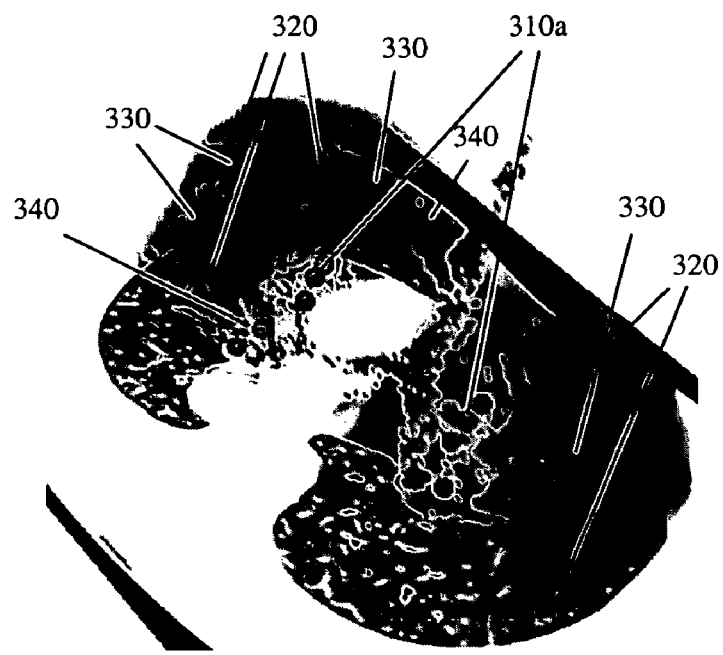
FIG. 3 is a pair of images illustrating a perfusion rendering along with a slice of CT data and the slice of CT data without rendering according to an exemplary embodiment of the present invention.
Figure 3B:
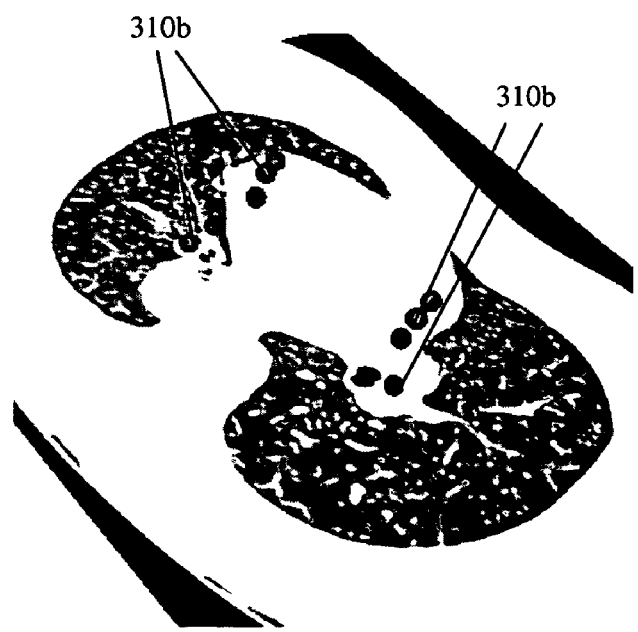

The perfusion map is generated by performing an adaptive smoothing of the segmented image using an averaging operator. The perfusion map is then rendered as a color-coded semi-transparent 3D volume (240). An example of this is shown in image (a) of FIG. 3. As shown in FIG. 3, image (a) is an original slice of CT data with the perfusion visualization overlaid. As shown in image (a) spheres 310a indicate the locations of pulmonary emboli, blue opaque patches 320 indicate areas of lower perfusion in the parenchyma, green semi-opaque patches 330 indicate areas of average perfusion and red transparent patches 340 indicate areas of high perfusion. In other words, patches 320 indicate areas that have a lack of blood flow, patches 330 indicate areas that have healthy or normal perfusion and patches 340 indicate areas that have increased densities or abnormally high perfusion.

As further shown in FIG. 3, image (b) is the original slice of CT data without perfusion rendering. In other words, image (b) is the original slice of CT data in a volumetric context with physician marked pulmonary emboli locations 310b. The marked pulmonary emboli locations 310b may also be obtained by a pulmonary embolism detection algorithm. The views of FIG. 3 and of FIG. 4 to be discussed below are made available to a medical practitioner by simply toggling between the original data and the color-coded data from a workstation or the operator's console 115.

Figure 4A:
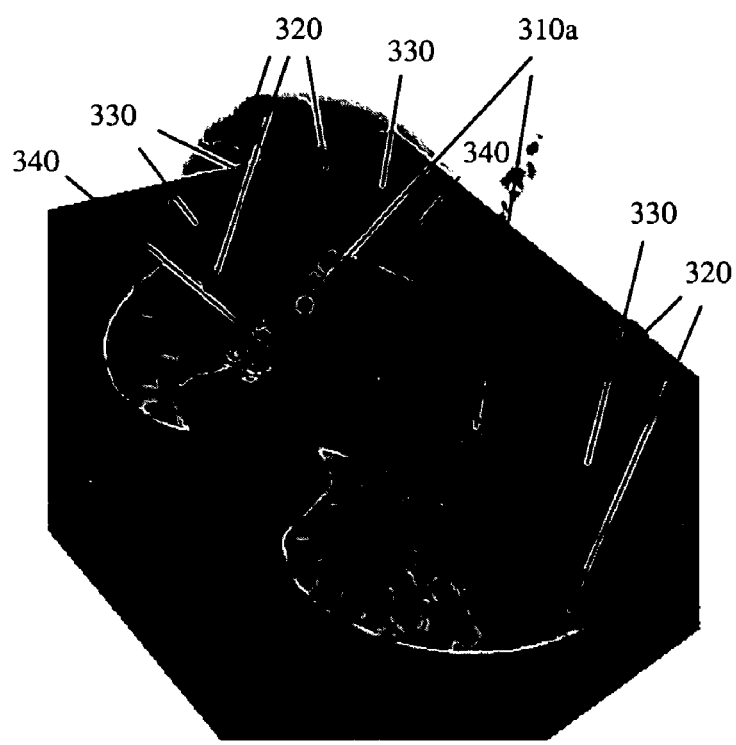
FIG. 4 is a pair of images illustrating a perfusion map of the slice of FIG. 3 with the 3D rendering and the perfusion map of the slice of FIG. 3 without rendering according to an exemplary embodiment of the present invention.
Figure 4B:
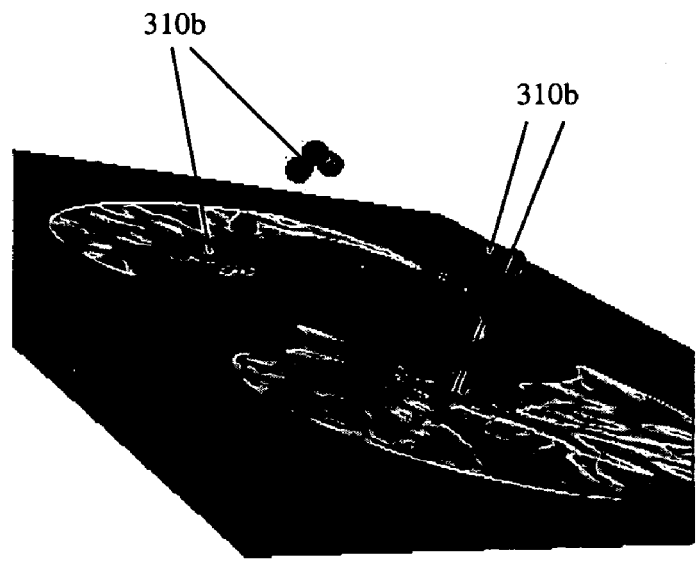

Image (a) of FIG. 4 illustrates a 2D view of the perfusion map with the 3D perfusion map overlaid. In addition, image (b) of FIG. 4 is a view of the image (a) with the 3D rendering toggled off thus enabling a 2D side view of the perfusion map. As can be gleaned from a review of the images of FIGS. 3 and 4, regions of the lung that are of the lowest perfusion are the most opaque and viewable regardless of the viewing angle.

Figure 5A:
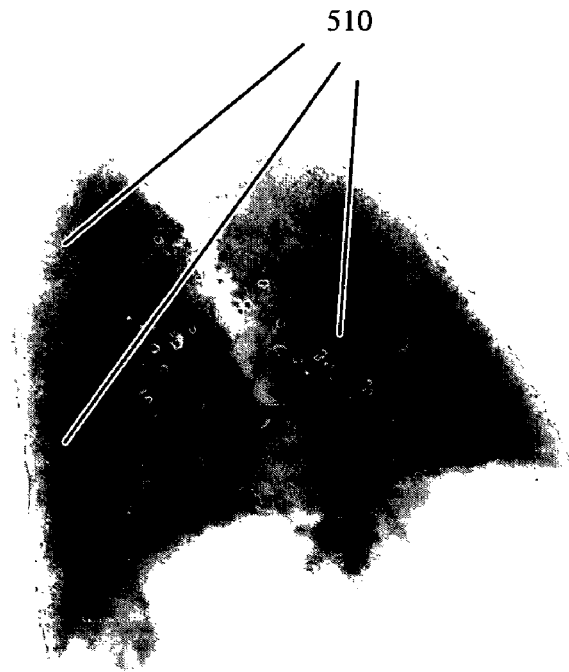
FIG. 5 is a pair of images illustrating a 3D visualization of a perfusion map for a patient who is negative for pulmonary embolism and for a patient who is positive for pulmonary embolism according to an exemplary embodiment of the present invention.
Figure 5B:
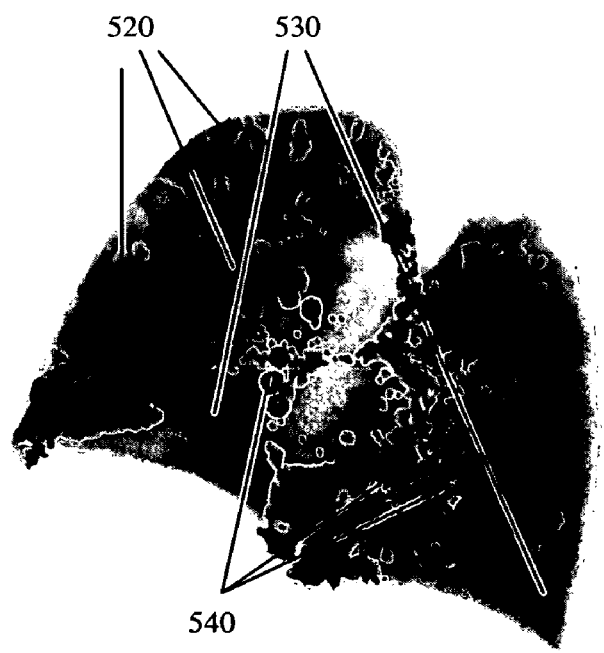

Thus, a medical practitioner can rapidly identify suspicious regions of low perfusion (e.g., regions affected by pulmonary emboli) in the lungs as shown, for example, by images (a) and (b) of FIG. 5. As shown in FIG. 5, image (a) is a 3D visualization of the perfusion map of a CTA for a patient who turned out to be negative for pulmonary embolism as indicated by patches 510 indicating homogeneous perfusion. Image (b) is a 3D visualization of the perfusion map of a CTA for a patient who turned out to be positive for pulmonary embolism as indicated by opaque patches 520 indicating low perfusion, transparent patches 530 indicating high perfusion and pulmonary emboli 540 marked by a medical practitioner.

The perfusion map computation will now be discussed in more detail. More specifically, the perfusion map is computed by determining the local-neighborhood mean densities of the lung parenchyma. This is accomplished by first segmenting the lung parenchyma and then performing a local smoothing.

Segmenting of the lung parenchyma consists of three steps: segmenting the lung volume from the thoracic volume; identifying the airways and blood vessels and removing the airways and vascular structures from the segmentation to create a mask of the parenchyma. The lung volume segmentation could be performed using a high-threshold region-growing, starting at a seed point within the trachea followed by a morphological closing. Basic thresholds could then be used to identify air and blood voxels within the segmented lung volume. For example, an upper threshold of −990 HU for air and a lower threshold of −300 HU for blood could be used. It should be understood that additional segmentation methods for identifying the airway and vascular trees may be utilized as a precise segmentation is not entirely necessary because a smoothing step will typically follow.

Once the parenchyma mask is available, the portions of the original CT volume that fall within this mask are adaptively smoothed. It should be understood that any smoothing/averaging operator can be used s long as subtracted air/blood voxels do not average into the smoothed parenchyma. In the example described below a 3D Gaussian kernel is used as the smoothing operator.

Figure 6:
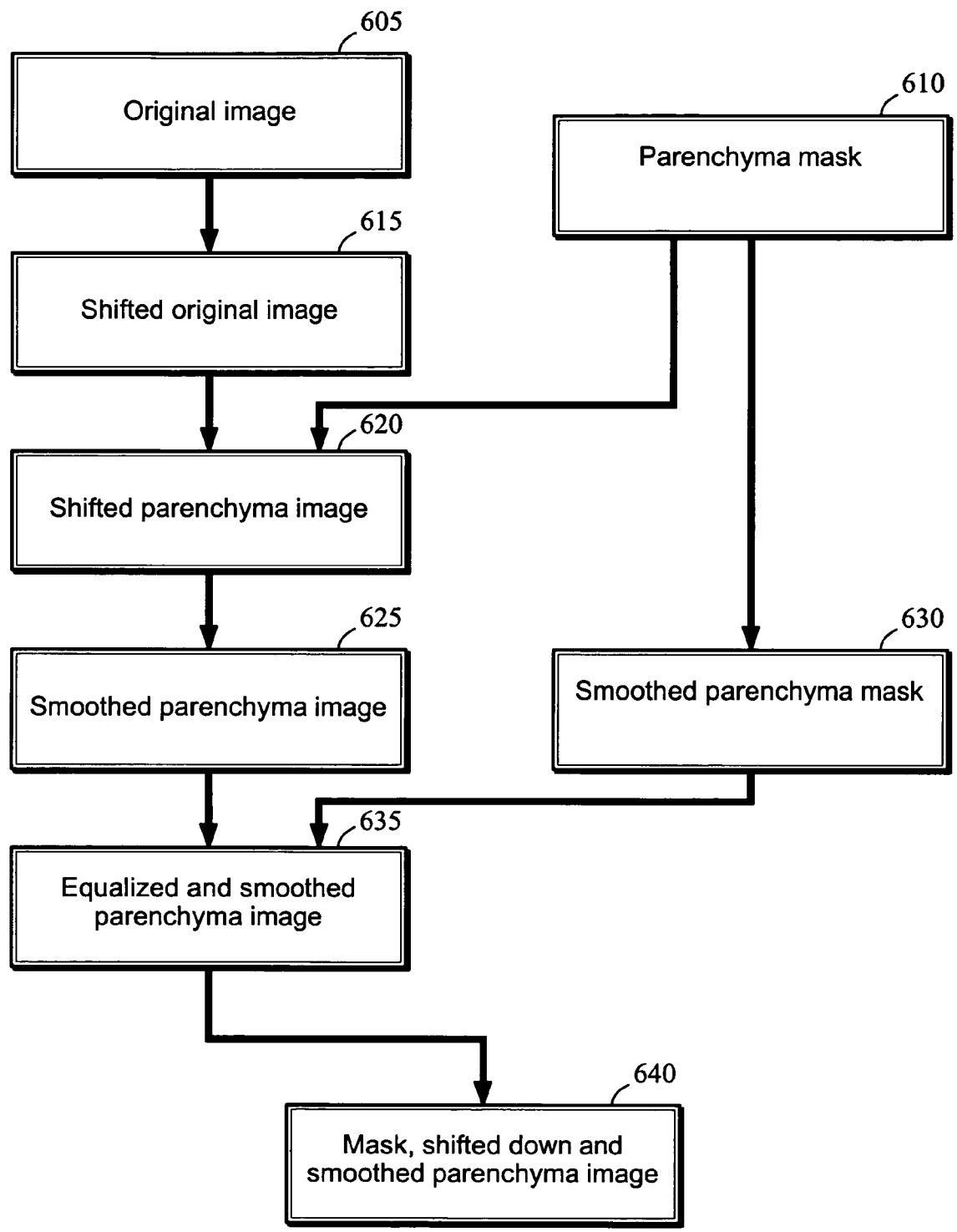
FIG. 6 is a flowchart illustrating a method for smoothing the lung parenchyma to create a perfusion map according to an exemplary embodiment of the present invention.

Exemplary steps for smoothing the lung parenchyma to create e perfusion map are shown in FIG. 6 and described as follows. First, shift up the original CT volume by 1024 HU so that –1024 HU becomes zero (605). Then, mask the shifted CT volume (615) with the parenchyma a mask (610) to obtain a shifted parenchyma image where all regions in the image that fall outside the mask are set to zero while all other regions retain their shifted values (620). A Gaussian smoothing is then performed on both the shifted parenchyma image and the parenchyma a mask to create a smoothed parenchyma image (625) and a smoothed parenchyma mask (630).

The smoothed parenchyma mask contains fractional values as opposed to binary values of the original parenchyma mask. The fractional values define what percentage of a specific voxel's smoothed value was obtained from the voxels within the mask as opposed to voxels outside the mask. The smoothed parenchyma mask is then equalized (635) by dividing each non-zero element by a corresponding element value in the smoothed parenchyma mask to produce an image that contains voxel values obtained solely from those with the mask. The resulting image is then masked with the original parenchyma mask and shifted down by 1024 HU so that element values again correspond to the HU scale (640).

Figure 7:
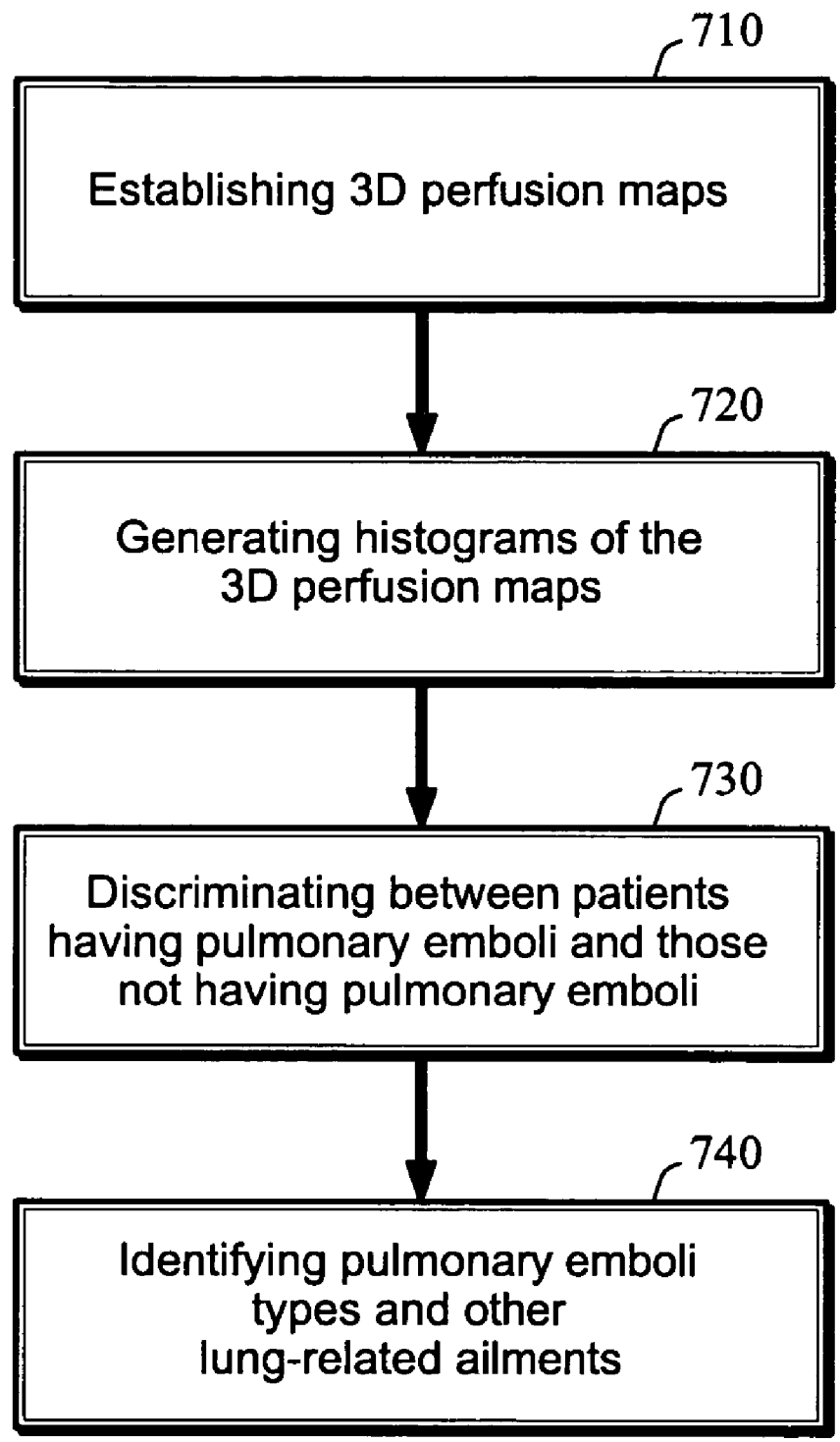
FIG. 7 is a flowchart illustrating a method for analyzing lung perfusion or density according to an exemplary embodiment of the present invention.

In addition to enabling a medical practitioner to identify suspicious regions of low perfusion, histograms of the perfusion map or multiple perfusion maps can be used to determine whether patients have a positive or negative presence of pulmonary emboli and help classify which types pulmonary emboli are present and whether patients have other conditions such as edema or pneumonia. FIG. 7 is a flowchart that illustrates one such method for analyzing lung perfusion according to an exemplary embodiment of the present invention.

Figure 8:
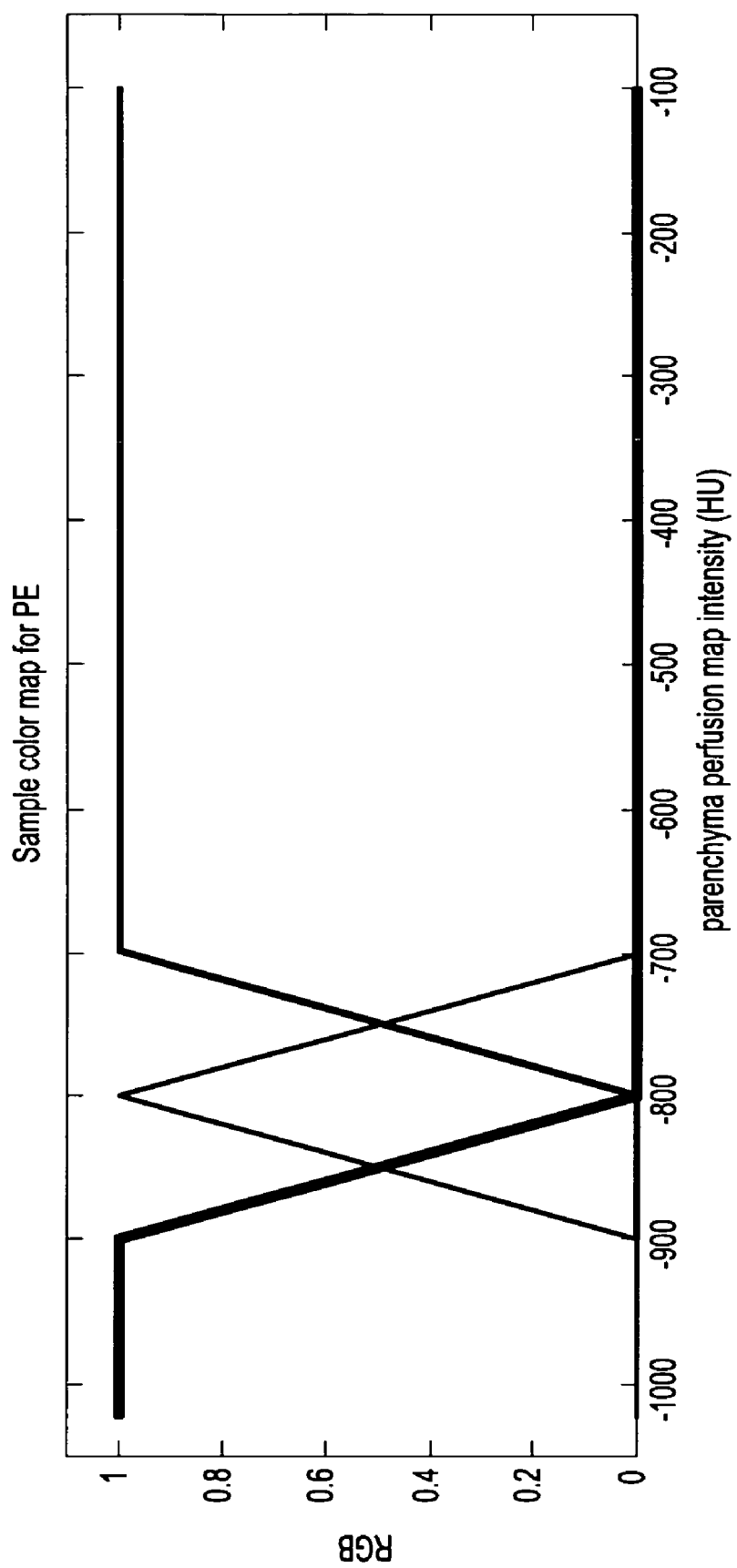
FIG. 8 is a plot illustrating a color map for pulmonary perfusion visualization according to an exemplary embodiment of the present invention.

As shown in FIG. 7, after generating perfusion maps in accordance with the above-mentioned techniques (710), a variety of histograms for a patient or patients are generated (720). Prior to generating and analyzing the histograms, a color map is used to color the values of the rendered perfusion map. An exemplary color map is shown in FIG. 8. According to the cold-to-hot color scheme shown in FIG. 8, normal perfusion is indicated by green, diminished perfusion by blue and high perfusion by red. A center value of –800 HU is shown and in this example was selected to yield a compromise between inter-patient comparability and to exploit the available color map intra-patient.

It is to be understood that the color map may be interactively translated and selected to have, for example, a 100 HU width or varying window settings such as a center of –900 HU to distinguish among areas of low perfusion or a center of –600 HU to distinguish among areas of high perfusion. Further, the center and window values may be adaptively set based upon values derived from a histogram analysis.

Figure 9A:
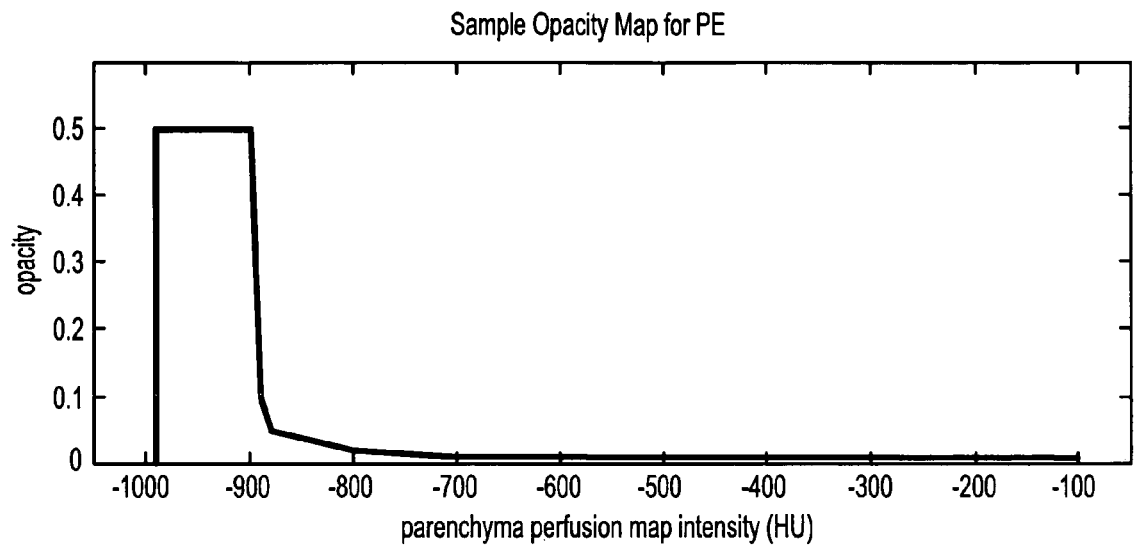
FIG. 9 is a pair of plots illustrating an opacity map for pulmonary perfusion visualization and for pulmonary perfusion visualization and edema according to an exemplary embodiment of the present invention.
Figure 9B:
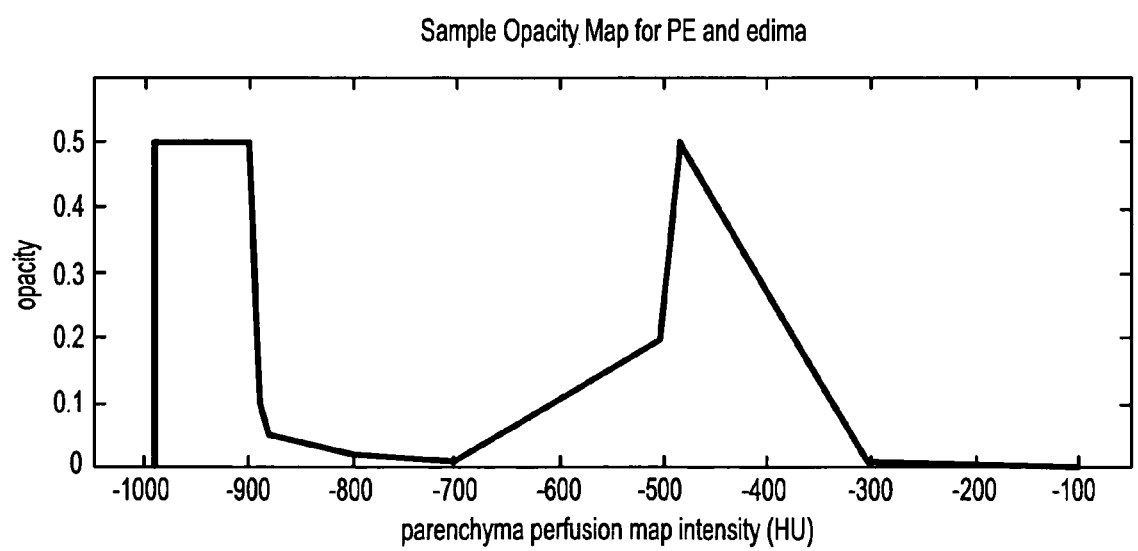

Using the settings defined by the color map, a piecewise linear opacity map of the perfusion maps can be generated. An exemplary piecewise linear opacity map is shown in plot (a) of FIG. 9. As shown in plot (a), areas of diminished perfusion are shown with substantially higher opacity than other parts of the parenchyma. In other words, the area from approximately –1000 HU to a bit higher than –900 HU is very opaque in a 3D perfusion rendered image. It is to be understood that this mapping may be interactively adjusted by a medical practitioner.

As an alternative, an opacity map that highlights areas of diminished perfusion and that highlights areas of the parenchyma with abnormally high density or perfusion can be generated. An example of such an opacity map is shown in plot (b) of FIG. 9. This map may be generated because areas of extremely high perfusion are opaque and they often signify problematic regions such as where there is a compression in the lung. It should also be understood that because a volume rendering is used to render the perfusion maps, opacity and color values can be adjusted on the fly. Further, any manual or automatic technique can be used to determine these values.

Figure 10B:
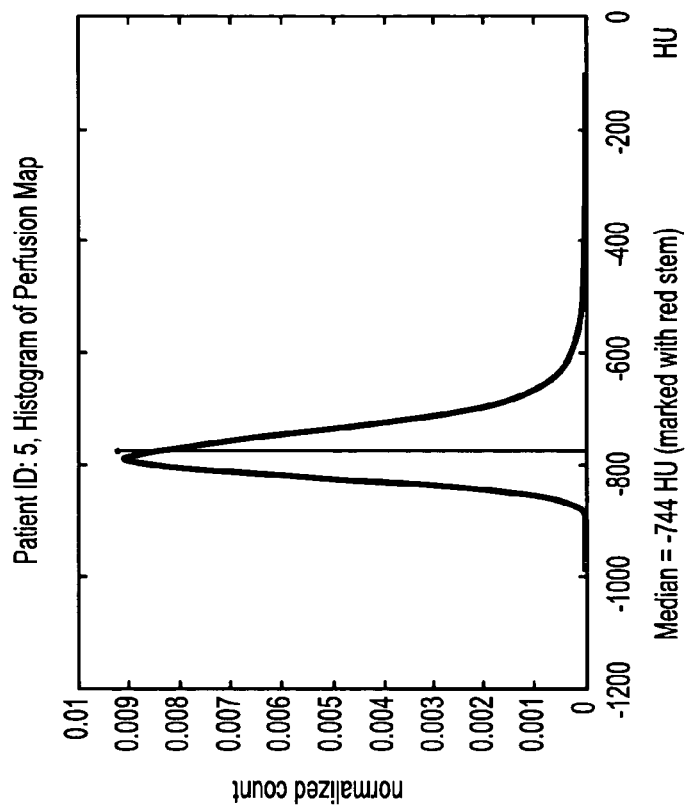
FIG. 10 is a pair of plots illustrating histograms of a perfusion map for a patient who is negative for pulmonary embolism and for a patient who is positive for pulmonary embolism according to an exemplary embodiment of the present invention.
Figure 10A:
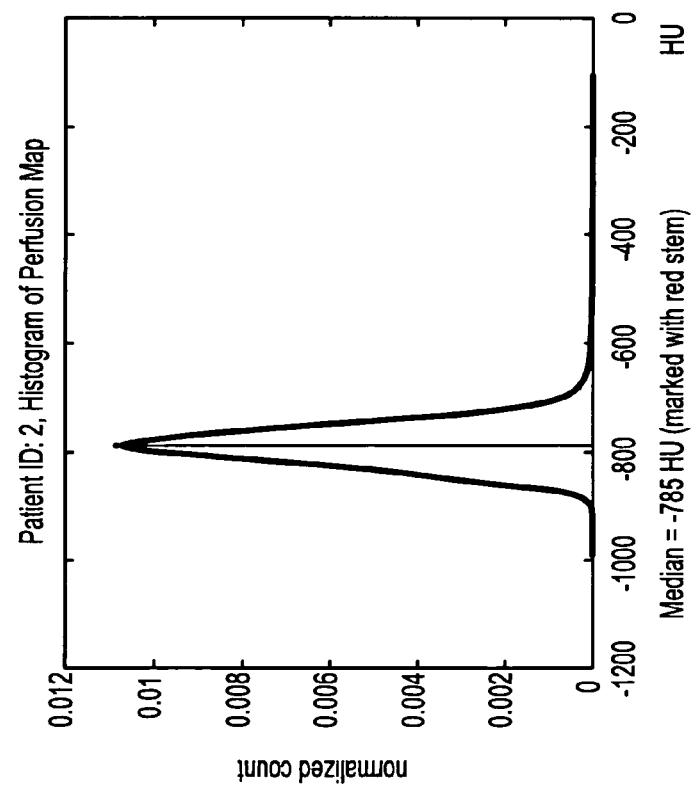

After generating the opacity maps, histograms of the perfusion maps may then be generated and analyzed. In analyzing the histograms, patients that are negative for pulmonary emboli tend to have parenchyma intensity distributions that are mostly symmetric with a low spread and hence could be characterized by their second and third moments. In addition, the maxima of pulmonary emboli negative histograms are typically located within a limited HU range. An example histogram for a patient who is negative for pulmonary emboli is shown in plot (a) of FIG. 10.

Figure 11B:
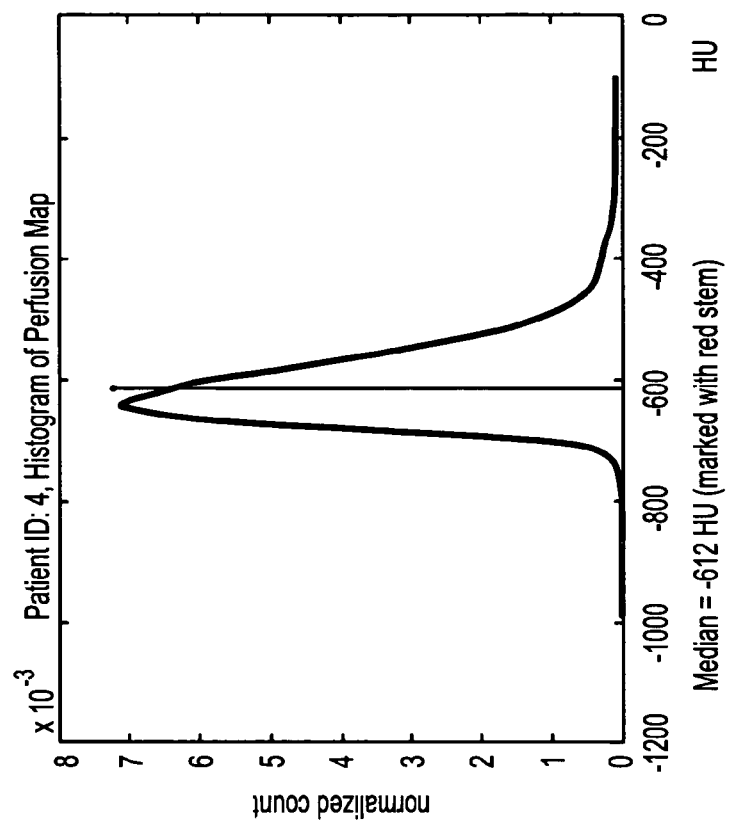
FIG. 11 is a pair of plots illustrating histograms of a perfusion map for a patient who has chronic pulmonary embolism and for a patient who has fluid-filled lungs according to an exemplary embodiment of the present invention.
Figure 11A:
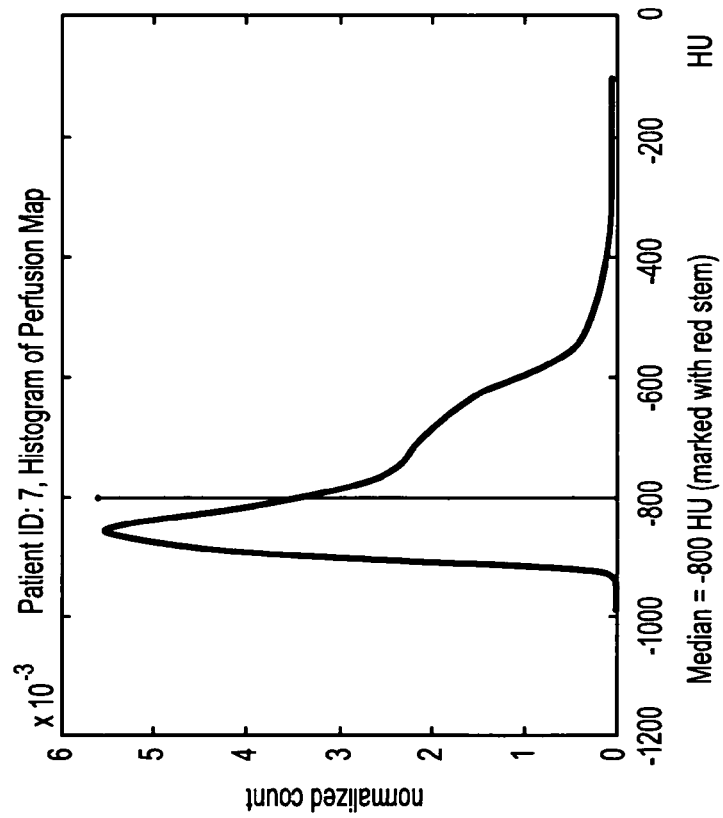

In further analyzing the histograms and/or extracting statistics therefrom, one may distinguish acute from chronic pulmonary emboli. This is possible because the perfusion distributions of the latter are extremely asymmetric with a large spread due to the characteristic pattern of mosaic attenuation. To illustrate this, example histograms of a patient who has acute pulmonary embolism, chronic pulmonary embolism and pulmonary embolism with edema or pneumonia are shown in plot (b) of FIG. 10 and plots (a) and (b) of FIG. 11 respectively.

Figure 12:
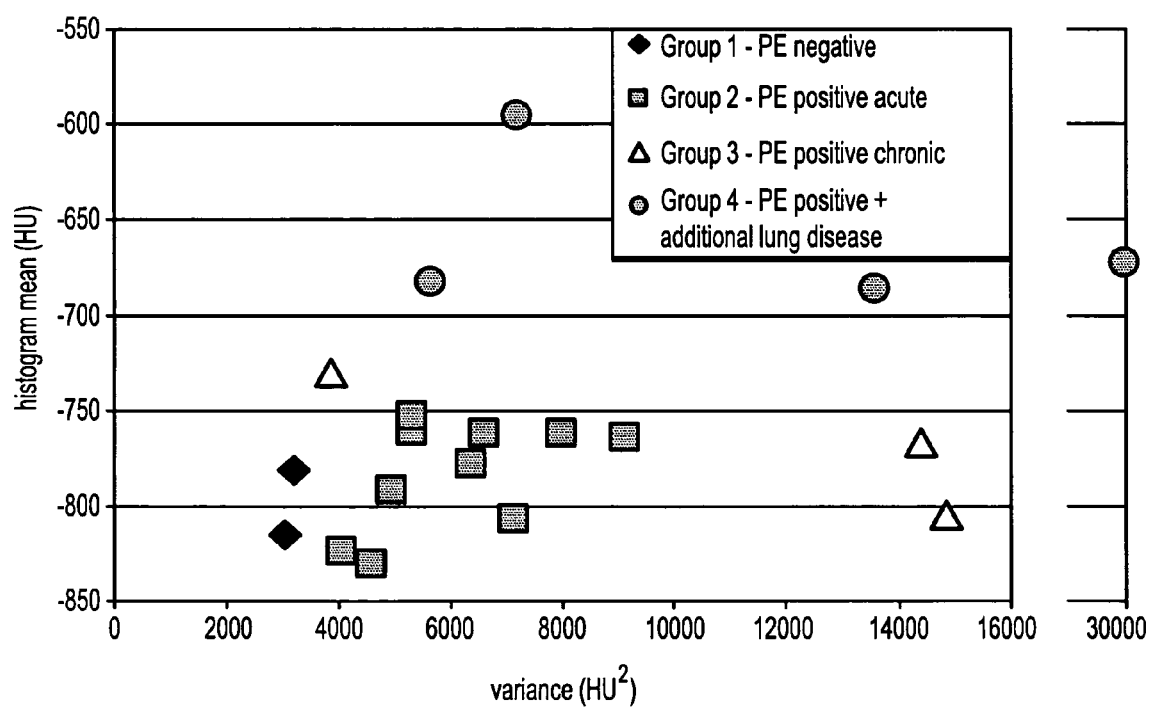
FIG. 12 is a scatter plot illustrating relating Hounsfeld (HU) values of histogram maximums to the variance of the perfusion maps for a number of patients for grouping the patients into certain disease categories according to an exemplary embodiment of the present invention.

Using the above data, positive and negative pulmonary embolism cases can be discriminated from each other (730) and conditions such as edema, acute and chronic pulmonary embolism may be identified (740). An example of how conditions such as edema, acute and chronic pulmonary embolism may be identified is shown by the scatter plot of FIG. 12. The scatter plot was created by relating the HU value of histogram maximums to the variance of the perfusion map for each patient. In particular, FIG. 12 illustrates a scatter plot for 19 patients referred for possible pulmonary embolism that were evaluated by CT following the administration of IV contrast media. The CT datasets were assessed by an experienced thoracic radiologist.

As shown in FIG. 12, 17 of the patients were diagnosed with multiple pulmonary emboli, while two were negative for pulmonary emboli. Patient having multiple pulmonary emboli had between 2 and 28 emboli with a median of 13 emboli per patient. As indicated, for example, by the legend in FIG. 12, three patients were diagnosed with chronic pulmonary embolism; however, only two of these patients had mosaic attenuation that results from long-term perfusion deficits associated with chronic pulmonary embolism. As further indicated by the legend in FIG. 12, the patients could be classified into four groups: pulmonary embolism (PE)-negative; PE positive acute; PE-positive chronic; and PE-positive and additional lung disease. The histograms of FIGS. 10 and 11 correspond to these four groups and the analysis thereof is what enabled the patients to be classified accordingly.

In accordance with an exemplary embodiment of the present invention, the perfusion map of the parenchyma is rendered as a color-coded semi-transparent 3D volume where regions of abnormally diminished perfusion are rendered relatively opaque. This facilitates rapid identification of regions suspicious for abnormal lung perfusion independent of viewing position and direction. Further, by extracting statistical features from the perfusion maps, these features can be used to distinguish patients with pulmonary embolisms from those without. For example, by identifying mosaic attenuation that is usually caused by chronic pulmonary embolism, chronic pulmonary embolism can be differentiated from acute pulmonary embolism. Moreover, because these features can be used to distinguish abnormalities in lung perfusion or density, they can be used to identify whether patients have additional conditions such as pneumonia or other types of diffuse lung disease.

It is to be further understood that the present invention may be implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

It is to be further understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It should also be understood that the above description is only representative of illustrative embodiments. For the convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be implemented without departing from the spirit and scope of the present invention.

It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A method for 3D visualization of a pair of lungs, comprising:
    segmenting image data of the pair of lungs and lung parenchyma;
    generating a 3D map as a function of the segmented image data; and
    rendering the 3D map to produce a visualization of a color-coded semi-transparent 3D volume in its entirety,
    wherein areas of low, average and high perfusion are represented by different degrees of opacity in the visualization of the 3D volume at the same time so that they can be differentiated from each other, and
    wherein the opacity is varied according to perfusion or density values in the 3D map overlaying a 2D slice of the image data with the color-coded semi-transparent 3D volume.

2. The method of claim 1, wherein the 3D map is one of a perfusion map or a density map.

3. The method of claim 1, wherein the 3D map is generated by one of adaptive smoothing or texture filtering.

4. The method of claim 1, wherein the area of low perfusion is an area that has a lack of blood flow, the area of average perfusion is an area that has healthy or normal perfusion, and the area of high perfusion is an area that has increased density or abnormally high perfusion.

5. The method of claim 4, wherein the area of low perfusion is due to an embolus.

6. The method of claim 1, further comprising:
    generating a histogram of the rendered 3D map; and
    determining whether the histogram indicates a positive or negative presence of embolus.

7. The method of claim 6, further comprising:
    classifying the embolus as one of acute or chronic.

8. A method for 3D visualization of lung perfusion, comprising:
    segmenting image data of lung parenchyma;
    generating a perfusion map of the segmented image data; and
    rendering the perfusion map to produce a visualization of a color-coded semi-transparent 3D volume in its entirety,
    wherein areas of low, average and high perfusion are represented by different degrees of opacity in the visualization of the 3D volume at the same time so that they can be differentiated from each other, and
    wherein the opacity is varied according to perfusion values in the perfusion map overlaying a 2D slice of the image data with the color-coded semi-transparent 3D volume.

9. The method of claim 8, wherein the step of generating a perfusion map of the segmented image data comprises:
    segmenting the lung parenchyma;
    performing a local smoothing; and
    determining local-neighborhood mean densities of the lung parenchyma.

10. The method of claim 9, wherein the step of segmenting the lung parenchyma comprises:
    segmenting a volume of the pair of lungs from a thoracic volume;
    identifying airways and blood vessels in the segmented lung volume; and
    generating a mask of the lung parenchyma by removing the airways and vascular structures from the segmented lung volume.

11. The method of claim 10, wherein the step of performing a local smoothing comprises:
    shifting unsegmented image data;
    masking the shifted image data with the parenchyma mask to obtain a shifted parenchyma image;
    performing a Gaussian smoothing on the parenchyma mask and the shifted parenchyma image to obtain a smoothed parenchyma mask and image;
    masking the smoothed parenchyma image with the smoothed parenchyma mask;
    equalizing the masked smoothed parenchyma image; and
    shifting the equalized image to generate the perfusion map.

12. The method of claim 8, wherein the areas of low and high perfusion are an indication of one of pulmonary embolus or diffuse lung disease.

13. The method of claim 8, wherein the image data is acquired using one of a CT, helical CT or MR imaging technique.

14. The method of claim 8, further comprising:
adjusting a color map to observe high density areas.

15. The method of claim 8, wherein the areas of low, average and high perfusion are further represented by different colors in the 3D volume.

16. A system for 3D visualization of a pair of lungs, comprising:
a memory device for storing a program;
a processor in communication with the memory device, the processor operative with the program to:
segment image data of the pair of lungs and lung parenchyma;
generate a 3D map as a function of the segmented image data; and
render the 3D map to produce a visualization of a color-coded semi-transparent 3D volume in its entirety,
wherein areas of low, average and high perfusion are represented by different degrees of opacity in the visualization of the 3D volume at the same time so that they can be differentiated from each other, and
wherein the opacity is varied according to perfusion or density values in the 3D map overlaying a 2D slice of the image data with the color-coded semi-transparent 3D volume.

17. The system of claim 16, wherein the 3D map is one of a perfusion map or a density map.

18. The system of claim 16, wherein the area of low perfusion is an area that has a lack of blood flow, the area of average perfusion is an area that has healthy or normal perfusion, and the area of high perfusion is an area that has increased density or abnormally high perfusion.

19. The system of claim 18, wherein the area of low perfusion is due to an embolus.

20. The system of claim 16, wherein the processor is further operative with the program to:
generate a histogram of the rendered 3D map; and
determine whether the histogram indicates a positive or negative presence of embolus.

21. The system of claim 20, wherein the processor is further operative with the program to:
classify the embolus as one of acute or chronic.

22. A system for 3D visualization of lung perfusion, comprising:
a memory device for storing a program;
a processor in communication with the memory device, the processor operative with the program to:
segment image data of lung parenchyma;
generate a perfusion map of the segmented image data; and
render the perfusion map to produce a visualization of a color-coded semi-transparent 3D volume in its entirety,
wherein areas of low, average and high perfusion are represented by different degrees of opacity in the visualization of the 3D volume at the same time so that they can be differentiated from each other, and
wherein the opacity is varied according to perfusion values in the perfusion map overlaying a 2D slice of the image data with the color-coded semi-transparent 3D volume.

23. The system of claim 22, wherein when generating a perfusion map of the segmented image data the processor is further operative with the program to:
segment the lung parenchyma;
perform a local smoothing; and
determine local-neighborhood mean densities of the lung parenchyma.

24. The system of claim 23, wherein when segmenting the lung parenchyma the processor is further operative with the program to:
segment a volume of the pair of lungs from a thoracic volume;
identify airways and blood vessels in the segmented lung volume; and
generate a mask of the lung parenchyma by removing the airways and vascular structures from the segmented lung volume.

25. The system of claim 24, wherein when performing a local smoothing the processor is further operative with the program to:
shift unsegmented image data;
mask the shifted image data with the parenchyma mask to obtain a shifted parenchyma image;
perform a Gaussian smoothing on the parenchyma mask and the shifted parenchyma image to obtain a smoothed parenchyma mask and image;
mask the smoothed parenchyma image with the smoothed parenchyma mask;
equalize the masked smoothed parenchyma image; and
shift the equalized image to generate the perfusion map.

26. The system of claim 22, wherein the areas of low and high perfusion are an indication of one of pulmonary embolus or diffuse lung disease.

27. The system of claim 22, wherein the image data is acquired using one of a CT, helical CT or MR imaging device.

28. The system of claim 22, the processor is further operative with the program to:
adjust a color map to observe high density areas.

29. The system of claim 22, wherein the areas of low, average and high perfusion are further represented by different colors in the 3D volume.

* * * * *